United States Patent [19]

Schossig et al.

[11] Patent Number: 5,068,468

[45] Date of Patent: Nov. 26, 1991

[54] HYDROGENATION OF ACETYLENIC ALCOHOLS

[75] Inventors: Juergen Schossig, Fussgoenheim; Gerhard Koppenhoffer, Roemerberg; Matthias Irgang, Heidelberg, all of Fed. Rep. of Germany; Rudi Schnur; George Roley, both of Baton Rouge, La.

[73] Assignee: BASF Atktiengesellschaft, Ludwigshafen, Fed. Rep. of Germany

[21] Appl. No.: 599,877

[22] Filed: Oct. 19, 1990

[51] Int. Cl.$^5$ .................... C07C 29/17; C07C 31/20
[52] U.S. Cl. .................................................. 568/861
[58] Field of Search ........................................ 568/861

[56] References Cited

U.S. PATENT DOCUMENTS

| 2,222,302 | 11/1940 | Schmidt et al. | 568/861 |
| 3,449,445 | 6/1969 | Wetherill | 260/635 |
| 3,998,758 | 12/1976 | Clyde et al. | 502/307 |
| 4,048,116 | 9/1977 | Voges et al. | 252/470 |
| 4,287,099 | 9/1981 | Baer et al. | 292/465 |

FOREIGN PATENT DOCUMENTS 382049  5/1990  European Pat. Off. .

*Primary Examiner*—Howard T. Mars
*Assistant Examiner*—Rebecca Cook
*Attorney, Agent, or Firm*—Keil & Weinkauf

[57] ABSTRACT

A process for the preparation of saturated alcohols by catalytic hydrogenation of acetylenic alcohols at a temperature of from 50° to 200° C. and under a pressure of from 30 to 320 bar, wherein use is made of a catalyst containing from 20 to 85% of nickel oxide, from 0 to 30% w/w of copper oxide, from 1 to 30% w/w of zirconium dioxide, from 1 to 30% w/w of silicon dioxide and from 1 to 30% w/w of aluminum oxide, by weight of the oxidic, unreduced catalyst.

3 Claims, No Drawings

HYDROGENATION OF ACETYLENIC ALCOHOLS

The present invention relates to a process for the preparation of saturated alcohols by catalytic hydrogenation of acetylenic alcohols.

Numerous catalysts for the hydrogenation of aliphatically unsaturated compounds have been described.

DE-A 2,536,276 discloses unsupported nickel catalysts for the industrial hydrogenation of butyne diol, which catalysts contain oxides of nickel, copper, molybdenum and manganese. The good results obtained with these catalysts under enhanced reaction conditions are achieved, however, at the expense of an increase in the formation of undesirable butanol.

U.S. Pat. No. 3,449,445 discloses catalysts containing nickel, copper and manganese on silicon dioxide. Continuous use of these catalysts in large-scale hydrogenation and purifying plants leads to deposition of silicon dioxide in heat exchangers and pipes. The resulting deposits can only be removed by carrying out very expensive cleaning operations.

EP-A 18,596 discloses a hydrogenation catalyst which contains the oxides of the metals nickel, copper, molybdenum and manganese and which produces particularly favorable results in the hydrogenation of 2-butyne-1,4-diol to butane-1,4-diol when the manufacture of the catalyst includes the step of adding an aluminum or iron salt prior to precipitation of the metal salts, after which the material is treated by filtering, washing, drying and tempering operations. However, this catalyst gradually disintegrates when used continuously in large-scale production plants.

It is thus an object of the present invention to provide a new, improved process for the hydrogenation of acetylenic alcohols which overcomes the above drawbacks.

Accordingly, we have found a novel and improved process for the preparation of saturated alcohols by catalytic hydrogenation of acetylenic alcohols at a temperature of from 50° to 200° C. and under a pressure of from 30 to 320 bar, wherein use is made of a catalyst containing from 20 to 85% of nickel oxide, from 0 to 30% w/w of copper oxide, from 1 to 30% w/w of zirconium dioxide, from 1 to 30% w/w of silicon dioxide and from 1 to 30% w/w of aluminum oxide, by weight of the oxidic, unreduced catalyst.

Examples of suitable catalysts are those which contain from 20 to 85% and preferably from 30 to 85% of NiO, from 0 to 30% and preferably from 0 to 20% and more preferably from 0 to 10% or substantially 0% of CuO, from 1 to 30% and preferably from 1 to 20% of $ZrO_2$, from 1 to 30% and preferably from 1 to 20% of $Al_2O_3$, and from 1 to 30% and preferably from 1 to 20% of $SiO_2$. The catalysts may also contain other oxides such as from 0 to 5% of $MoO_3$ and from 0 to 5% of $MnO_2$, the above percentages being based on the weight of the oxidic, unreduced catalyst.

Basically, the preparation of said saturated, in particular dihydric, alcohols may be carried out starting from any acetylenic alcohol as obtained by usual methods, for example 2-butyne-1,4-diol or propargyl alcohol.

The present process is particularly suitable for the hydrogenation of 2-butyne-1,4-diol to butane-1,4-diol, in which it achieves a considerable increase in the throughput rate and a significant prolongation of the onstream time.

The catalysts suitable for use in the process of the invention are prepared, for example, by precipitating the said salts of the metals nickel, copper, zirconium, aluminum, silicon and, perhaps, molybdenum and manganese in the usual way from an aqueous solution at a temperature of from 30° to 90° C. and a pH of from 5 to 9 and then filtering the suspension, drying the filter cake and tempering the dried material at a temperature of from 300° to 700° C., the molybdenum being added in the form of ammonium molybdate prior to the drying stage. Precipitation is effected by mixing an aqueous solution of salts, e.g. nitrates, sulfates or acetates, of the said metals nickel, copper, zirconium, aluminum, silicon and, perhaps, manganese with an aqueous solution of an alkali metal carbonate. The proportions of said metal salts used are such that the tempered catalyst material has the desired composition as defined above.

The water-soluble salts of zirconium, aluminum and silicon may be replaced, either partially or completely, for example by solid or pre-precipitated $ZrO_2$, $Al_2O_3$, $SiO_2$ or alumosilicate, and these are added to the aqueous metal salt solution prior to precipitation or are placed in the stirred vessel as first components or are produced in a pre-precipitation stage or are added to the suspension following precipitation.

More specifically, the catalyst may be prepared, for example, by stirring the aqueous solution of salts of nickel, copper and zirconium with an aqueous alkali metal carbonate solution so as to deposit said metals in the form of their hydroxides and carbonates onto $Al_2O_3$ or $SiO_2$ produced in a previous stage by a precipitation technique. The metal salt content is advantageously from 30 to 40% w/w, and the concentration of the alkali metal carbonate solution is, for example, from 15 to 20% w/w. Precipitation is carried out at a temperature of from 20° to 90° C. and preferably from 35° to 80° C. and at a pH of from 5 to 9 and preferably from 6 to 8.

The suspension thus obtained is filtered and then washed with water until no more anions can be detected in the washings. The filter cake is then dried at, say, from 120° to 200° C. in a drying cabinet or spray drier. The molybdenum is preferably added to the moist filter cake in the form of ammonium heptamolybdate. The dried filter cake is tempered at a temperature of from 350° to 700° C. and preferably from 400° to 600° C.

It is convenient to pellet or extrude the catalyst material in the usual manner before use. For example, the catalyst material is compressed together with a pelleting agent, such as graphite, in a pelleting press. The pellets measuring $5.0 \times 3.0$ mm have an apparent density of from 1,000 to 1,500 g/l, a porosity of from 0.2 to 0.6 $cm^3/g$ (as measured by water absorption) and a hardness of from 2,000 to 5,000 $N/cm^2$.

Extrudates may be formed from the catalyst material by mixing it with water and possibly an acid, preferably formic acid or nitric acid, and kneading and extruding the mixture, which is dried and then tempered at 500° C. In general, catalysts of lighter weight are obtained by this method.

Prior to their use in the hydrogenation of acetylenic alcohols, the resulting catalysts are subjected to conventional pretreatment. For example, such pretreatment may consist in heating the catalyst for from about 20 to 40 hours at a temperature of from 150° to 500° C. and preferably from 250° to 500° C. under a hydrogen pressure of from 1 to 300 bar and preferably from 100 to 150 bar. The hydrogenation catalyst in its reduced form shows a degree of reduction of at least 50% based on the hydrogenating metals. To reduce the hazards involved in handling the catalyst in air, the reduction treatment is advantageously followed by surface passivating treatment with a nitrogen/oxygen mixture at a temperature of from 10° to 80° C. and preferably from 40° to 60° C.

The hydrogenation of said unsaturated compounds is carried out in the temperature and pressure ranges stated in, say, a reactor containing the catalyst in the form of a fixed bed.

As seen from the following Examples, our process achieves, surprisingly, considerably higher space-time yields and longer on-stream times than is the case with prior art processes.

EXAMPLES

In the following Examples, the percentages are by weight.

PREPARATION OF CATALYST

Example 1

Solution 1

22.5 g of $Al_2O_3$ in the form of aluminum sulfate were dissolved in 187 ml of water with the addition of 24 ml of concentrated sulfuric acid.

Solution 2

250 g of waterglass solution (27% of $SiO_2$) were dissolved in 864 g of water.

Solution 3

This solution was formed by combining solutions 1 and 2. Its pH was 1.5.

1,200 ml of water were placed in a stirred vessel having a capacity of 10 liters, and solution 3 was added thereto together with 140 g of concentrated $NH_4OH$ at a temperature of 40° C. to cause precipitation, the $NH_4OH$ being added at such a rate that a pH of 7.5 was maintained throughout precipitation. Stirring was continued for a further 5 minutes. There were then added, over a period of 45 minutes, 1,466 g of an aqueous solution containing nickel nitrate (equivalent to 337.5 g of NiO) and zirconium acetate (equivalent to 22.5 g of $ZrO_2$) concurrently with a total of 3,000 g of 20% soda solution at a pH of 6.0 and a temperature of 40° C. to effect further precipitation. On completion of precipitation, air was passed through the suspension with vigorous stirring over a period of 60 minutes.

The suspension thus obtained was filtered, and the filter cake was washed with demineralized water until the electrical conductivity of the washings was about 20 μs. The filter cake was then dried at a temperature of 150° C. before it was tempered at a temperature of 500° C. over a period of 4 hours.

The resulting catalyst had the following composition: 75% of NiO, 15% of $SiO_2$, 5% of $Al_2O_3$, 5% of $ZrO_2$.

The catalyst powder was mixed with 3% of graphite and formed into pellets measuring 5×3 mm. The pellets had a porosity of 0.26 ml/g (as measured by water absorption) and a hardness of 4,500 $N/cm^2$.

The shaped catalyst was then reduced at a temperature of 450° C. and a hydrogen pressure of 250 bar over a period of 20 hours. After it had cooled to room temperature, it was subjected to surface pacifying treatment with an $N_2/O_2$ mixture. Care was taken to ensure that the temperature did not rise above 60° C. during said pacifying treatment.

HYDROGENATION OF ACETYLENIC ALCOHOLS

Example 2

The catalyst obtained in Example 1 was packed into a hydrogenation reactor. At a temperature of 150° C. and a hydrogen pressure of 250 bar there were hydrogenated 5 parts by weight of a 50% aqueous solution of 2-butyne-1,4-diol with 2,500 parts by volume (STP) of hydrogen per 8 parts by volume of catalyst per hour. In order to maintain a steady temperature in the reactor and to ensure that the liquid was evenly distributed over the catalyst bed, the butyne diol feed was diluted with 50 parts by volume of effluent per hour. The heat of hydrogenation was removed via a heat exchanger located in the liquid circuit. Following the removal of the gaseous phase from the liquid phase, the excess gas was replenished with fresh hydrogen and recycled to the reactor inlet.

The conversion of the 2-butyne-1,4-diol was virtually quantitative.

The by-products obtained in the above hydrogenation were inter alia:

| | |
|---|---|
| butanol | <5% |
| 2-methylbutane-1,4-diol | <0.2% |
| 2-butyne-1,4-diol | <0.1% |
| [2-(4-hydroxy)butoxy]oxalene | <0.3% |
| 4-hydroxybutyraldehyde | <0.5% |
| γ-butyrolactone | <0.5% | the percentages being based on the anhydrous compounds.

The discharged product contained at least 94% of butane-1,4-diol (based on the anhydrous compound) and was worked up to pure butane-1,4-diol by distillation.

The throughput rate of butyne diol in Example 2 is two to three times that achieved in a comparative test using the catalyst described in EP-A 18,569.

EXAMPLE 3

The hydrogenation described in Example 2 was prolonged. After an onstream time of about 2 months, the hydrogenating efficiency of the catalyst was found to have deteriorated, this being mainly due to deposition of inorganic components originally contained in the commercial butyne diol solution used. The catalyst bed was washed with warm water (30° C.) for 24 hours. Following this treatment, the catalyst again had approximately its original activity. The washings contained chiefly silicon (0.1% w/w) and sodium (0.03% w/w) in addition to some organic components (<5% w/w).

We claim:

1. A process for the preparation of saturated alcohols by catalytic hydrogenation of acetylenic alcohols at a temperature of from 50° to 200° C. and under a pressure of from 30 to 320 bar, wherein use is made of a catalyst containing from 20 to 85% of nickel oxide, from 0 to 30% w/w of copper oxide, from 1 to 30% w/w of zirconium dioxide, from 1 to 30% w/w of silicon dioxide and from 1 to 30% w/w of aluminum oxide, by weight of the oxidic, unreduced catalyst.

2. A process as claimed in claim 1, wherein butane-1,4-diol is prepared from 2-butyne-1,4-diol.

3. A process as claimed in claim 1, wherein, following a reduction in catalyst activity, the catalyst is reactivated by treatment with water at a temperature of from 20° to 200° C. under a pressure of from 100 to 200 bar.

* * * * *

UNITED STATES PATENT AND TRADEMARK OFFICE
CERTIFICATE OF CORRECTION

PATENT NO. : 5,068,468

DATED : November 26, 191

INVENTOR(S) : Juergen SCHOSSIG et al.

It is certified that error appears in the above-identified patent and that said Letters Patent is hereby corrected as shown below:

<u>On the Cover Page</u>

The second named inventor should read --Koppenhoefer--

Signed and Sealed this

Twenty-seventh Day of April, 1993

Attest:

MICHAEL K. KIRK

Attesting Officer     Acting Commissioner of Patents and Trademarks